(12) United States Patent
Yamashita et al.

(10) Patent No.: US 12,372,675 B2
(45) Date of Patent: Jul. 29, 2025

(54) RADIATION DETECTOR AND RADIATION CT APPARATUS

(71) Applicant: CANON KABUSHIKI KAISHA, Tokyo (JP)

(72) Inventors: Takanori Yamashita, Tokyo (JP); Tatsuya Ryoki, Kanagawa (JP); Masanobu Ohmura, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 317 days.

(21) Appl. No.: 18/194,719

(22) Filed: Apr. 3, 2023

(65) Prior Publication Data
US 2024/0302547 A1    Sep. 12, 2024

(30) Foreign Application Priority Data
Mar. 7, 2023 (JP) ................. 2023-034933

(51) Int. Cl.
*G01T 1/24* (2006.01)
*A61B 6/03* (2006.01)
*A61B 6/42* (2024.01)

(52) U.S. Cl.
CPC .............. *G01T 1/247* (2013.01); *A61B 6/035* (2013.01); *A61B 6/4233* (2013.01)

(58) Field of Classification Search
CPC ........ G01T 1/247; A61B 6/035; A61B 6/4233
See application file for complete search history.

(56) References Cited

U.S. PATENT DOCUMENTS

| | | | |
|---|---|---|---|
| 6,242,746 B1 * | 6/2001 | Teranuma | H10F 39/195 257/E27.111 |
| 7,223,982 B1 | 5/2007 | Chen | |
| 2002/0000549 A1 | 1/2002 | Spartiotis | |
| 2011/0155892 A1 * | 6/2011 | Neter | H04N 25/59 250/208.1 |
| 2024/0298982 A1 * | 9/2024 | Uchida | G01T 1/247 |

FOREIGN PATENT DOCUMENTS

| | | | | |
|---|---|---|---|---|
| CN | 101884087 A | * | 11/2010 | ............ H01J 43/18 |
| DE | 102017124077 A1 | * | 4/2019 | ........... G01N 23/046 |
| JP | 9-92806 A | | 4/1997 | |
| JP | 11-287862 A | | 10/1999 | |
| JP | 2001-506405 A | | 5/2001 | |
| WO | WO 2017/122514 A1 | * | 7/2017 | ........... H10F 39/809 |

OTHER PUBLICATIONS

U.S. Appl. No. 18/297,178, filed Apr. 7, 2023, Tatsuya Ryoki.

* cited by examiner

Primary Examiner — Edwin C Gunberg
Assistant Examiner — Richard O Toohey
(74) Attorney, Agent, or Firm — VENABLE LLP

(57) ABSTRACT

A radiation detector obtained by arranging a plurality of pixels on a semiconductor substrate configured to convert incident radiation into charges is provided. The plurality of pixels comprise a plurality of first pixels, and a plurality of second pixels arranged along an outer edge of the semiconductor substrate. Each of the plurality of second pixels has output sensitivity higher than output sensitivity of each of the plurality of first pixels. An interval between adjacent second pixels among the plurality of second pixels is smaller than an interval between adjacent first pixels among the plurality of first pixels.

34 Claims, 7 Drawing Sheets

RADIATION DETECTOR AND RADIATION CT APPARATUS

BACKGROUND OF THE INVENTION

Field of the Invention

The present invention relates to a radiation detector and a radiation CT apparatus.

Description of the Related Art

There is known that a semiconductor substrate which converts incident radiation into charges is used for a radiation detector. U.S. Pat. No. 7,223,982 describes a structure in which the side surface of a semiconductor substrate is covered with an insulator and a cathode electrode is provided to extend over part of the side surface covered with the insulator in order to suppress a decrease in charge collection efficiency in an end portion of the semiconductor substrate to cause deterioration in image quality.

In the structure described in U.S. Pat. No. 7,223,982, since part of the side surface of the thin semiconductor substrate is covered with the cathode electrode, a manufacturing step may become complicated.

Some embodiments of the present invention provide a technique advantageous in suppressing a decrease in charge collection efficiency in an end portion of a semiconductor substrate.

SUMMARY OF THE INVENTION

According to some embodiments, a radiation detector obtained by arranging a plurality of pixels on a semiconductor substrate configured to convert incident radiation into charges, wherein the plurality of pixels comprise a plurality of first pixels, and a plurality of second pixels arranged along an outer edge of the semiconductor substrate, each of the plurality of second pixels has output sensitivity higher than output sensitivity of each of the plurality of first pixels, and an interval between adjacent second pixels among the plurality of second pixels is smaller than an interval between adjacent first pixels among the plurality of first pixels, is provided.

According to some other embodiments, a radiation detector obtained by arranging a plurality of pixels on a semiconductor substrate configured to convert incident radiation into charges, wherein the plurality of pixels comprise a plurality of first pixels, and a plurality of second pixels arranged along an outer edge of the semiconductor substrate, each of the plurality of pixels comprises an electrode arranged on one principal surface out of two principal surfaces of the semiconductor substrate, an area of the electrode of each of the plurality of second pixels is larger than an area of the electrode of each of the plurality of first pixels, and an interval between adjacent electrodes among the electrodes of the plurality of second pixels is smaller than an interval between adjacent electrodes among the electrodes of the plurality of first pixels, is provided.

According to still other embodiments, a radiation detector obtained by arranging a plurality of pixels on a semiconductor substrate configured to convert incident radiation into charges, wherein the plurality of pixels comprise a plurality of first pixels, and a plurality of second pixels arranged along an outer edge of the semiconductor substrate, signals of the plurality of first pixels are output as a first signal based on a signal value of a signal output from at least one pixel among the plurality of first pixels, signals of the plurality of second pixels are output as a second signal based on signal values of signals output from at least two pixels among the plurality of second pixels, and the number of pixels used to generate the second signal among the plurality of second pixels is larger than the number of pixels used to generate the first signal among the plurality of first pixels, is provided.

Further features of the present invention will become apparent from the following description of exemplary embodiments (with reference to the attached drawings).

DESCRIPTION OF THE EMBODIMENTS

Figure 1:
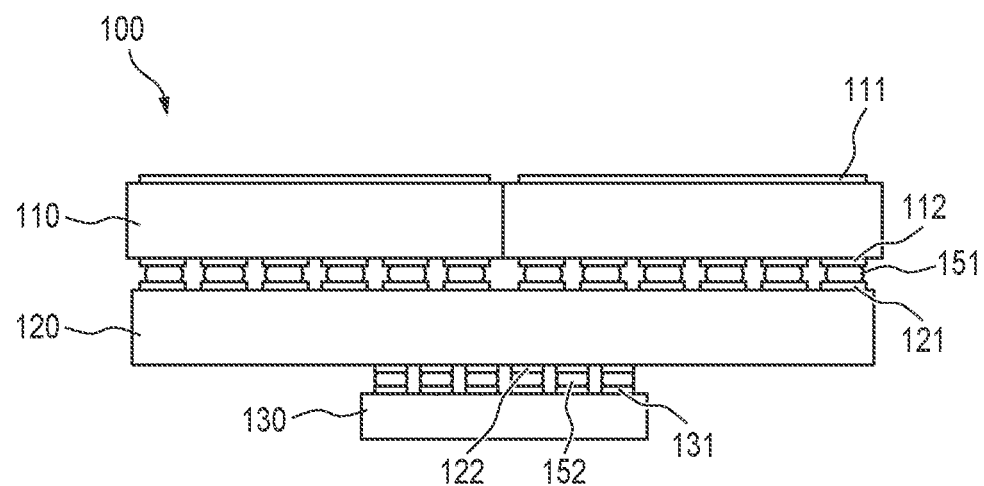
FIG. 1 is a view showing an example of the arrangement of a radiation detector according to an embodiment.

Hereinafter, embodiments will be described in detail with reference to the attached drawings. Note, the following embodiments are not intended to limit the scope of the claimed invention. Multiple features are described in the embodiments, but limitation is not made to an invention that requires all such features, and multiple such features may be combined as appropriate. Furthermore, in the attached drawings, the same reference numerals are given to the same or similar configurations, and redundant description thereof is omitted.

Radiation according to the present invention can include not only α-rays, β-rays, and γ-rays that are beams generated by particles (including photons) emitted by radioactive decay but also beams having equal or more energy, for example, X-rays, particle rays, and cosmic rays.

A radiation detector according to an embodiment of the present invention will be described with reference to FIGS.

1 to 12. FIG. 1 is a view showing an example of the arrangement of a radiation detector 100 according to this embodiment. The radiation detector 100 includes a semiconductor substrate 110 that converts incident radiation into charges, an interposer 120, and an integrated circuit 130. For the semiconductor substrate 110, a semiconductor single crystal substrate of a cadmium zinc telluride, cadmium telluride, or the like that directly converts incident radiation into charges is used. Note that this embodiment will mainly explain cadmium zinc telluride (CdZnTe) and cadmium telluride (CdTe) but the present invention is not limited to this form and can be applied to a semiconductor single crystal substrate that can directly detect radiation such as X-rays. For example, this embodiment can be applied to a semiconductor single crystal substrate of lead iodide ($PbI_2$), mercury iodide ($HgI_2$), bismuth iodide ($BiI_3$), thallium bromide (TlBr), or the like. The interposer 120 electrically connects pixels arranged on the semiconductor substrate 110 and the integrated circuit 130. The integrated circuit 130 controls the operations of the pixels arranged on the semiconductor substrate 110 and processes a signal output from each pixel. The integrated circuit 130 is, for example, a semiconductor device such as an ASIC (Application Specific Integrated Circuit). Electrodes 112 arranged on a principal surface facing the interposer 120 out of two principal surfaces of the semiconductor substrate 110 and terminals 121 of the interposer 120 are electrically connected to each other via conductive members 151 such as solder balls, respectively. Terminals 122 of the interposer 120 and terminals 131 of the integrated circuit 130 are electrically connected to each other via conductive members 152 such as solder balls, respectively.

In the radiation detector 100, a plurality of pixels are arranged on the semiconductor substrate 110 that converts incident radiation into charges. Each of the plurality of pixels includes the individual electrode 112 arranged on one of the two principal surfaces of the semiconductor substrate 110, and this electrode 112 can define the position of each pixel. On the other principal surface out of the two principal surfaces of the semiconductor substrate 110, an electrode 111 is arranged, as shown in FIG. 1. The electrode 111 may be formed integrally to cover the entire principal surface of the semiconductor substrate 110, as shown in FIG. 1, or may be formed individually for each pixel like the electrodes 112. In this embodiment, the electrode 112 functions as an anode electrode and the electrode 111 functions as a cathode electrode. However, the electrode 112 may function as a cathode electrode and the electrode 111 may function as an anode electrode. Although not shown in FIG. 1, the electrode 111 is also electrically connected to the integrated circuit 130, similar to the electrode 112. The electrode 111 may be connected to the integrated circuit 130 via the interposer 120 or may be connected to the integrated circuit 130 without intervention of the interposer 120.

When a voltage is applied between the electrodes 111 and 112 and electrons and holes generated by incidence of radiation are swept, the electric field is reduced in the pixel in an end portion of the semiconductor substrate 110, thereby decreasing the charge collection efficiency. The decrease in the charge collection efficiency in the pixel in the end portion of the semiconductor substrate 110 may cause deterioration in image quality of an obtained radiation image. To suppress the decrease in the charge collection efficiency in the pixel in the end portion of the semiconductor substrate 110, the pixel arranged in the end portion of the semiconductor substrate 110 has an arrangement of suppressing the decrease in the charge collection efficiency, as compared with the remaining pixels.

For example, the radiation detector 100 may be configured so that the output sensitivity of each of the pixels arranged in the outer edge portion of the semiconductor substrate 110 is higher than that of each of the remaining pixels surrounded by the pixels arranged in the outer edge portion. If the output sensitivity of pixel A is higher than that of pixel B, this means that the signal value of a signal output from pixel A is larger than the signal value of a signal output from pixel B when charges are uniformly generated in the semiconductor substrate 110 on which pixels A and B are arranged. That is, the output sensitivity can be a value representing the charge collection efficiency with respect to charges converted from radiation in each pixel. Therefore, this is different from sensitivity correction by correction of the signal value such as offset correction or shading correction performed in the succeeding stage of the radiation detector 100.

Figure 2:
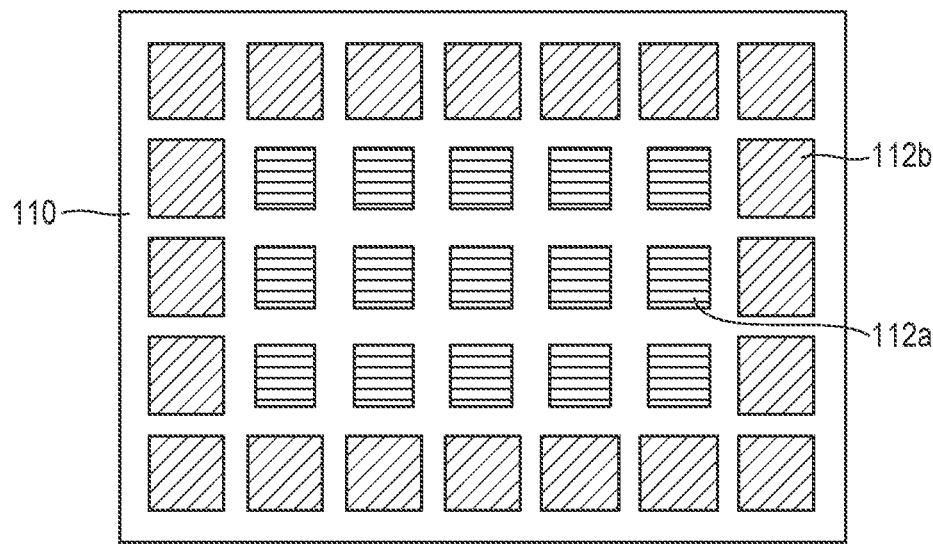
FIG. 2 is a view showing an example of the arrangement of electrodes arranged on a semiconductor substrate of the radiation detector shown in FIG. 1.

FIG. 2 is a view showing an example of the arrangement of the electrodes 112 arranged on the semiconductor substrate 110. The plurality of pixels include a plurality of first pixels whose positions are defined by electrodes 112a, respectively, and a plurality of second pixels whose positions are defined by electrodes 112b arranged along the outer edge of the semiconductor substrate 110 to surround the plurality of first pixels. As shown in FIG. 2, the plurality of second pixels (electrodes 112b) can be pixels arranged at positions closest to the outer edge of the semiconductor substrate 110 among the plurality of pixels arranged on the semiconductor substrate 110. In the following description, the plurality of second pixels arranged along the outer edge of the semiconductor substrate 110 will sometimes be referred to as the electrodes 112b (with an oblique stripe pattern) hereinafter. Similarly, the plurality of first pixels surrounded by the plurality of second pixels will sometimes be referred to as the electrodes 112a (with a horizontal stripe pattern) hereinafter.

The area of the electrode 112b of each of the plurality of second pixels is larger than the area of the electrode 112a of each of the plurality of first pixels. Thus, the output sensitivity of each second pixel (electrode 112b) is higher than that of each first pixel (electrode 112a), thereby making it possible to suppress the decrease in the charge collection efficiency in the second pixel (electrode 112b) arranged in the end portion of the semiconductor substrate 110.

As shown in FIG. 2, even if the electrodes 112 have different areas, they may be arranged at an equal pitch in the row direction (for example, the horizontal direction in FIG. 2) and the column direction (for example, the vertical direction in FIG. 2) intersecting the row direction. More specifically, the distances between the centers (which can be, for example, the geometric centroid positions of the electrodes 112 in orthogonal projection to the principal surface of the semiconductor substrate 110, and will sometimes simply be referred to as the centroid positions hereinafter) of the electrodes 112b of the second pixels along the outer edge of the semiconductor substrate 110 and the centroid positions of the electrodes 112a of the first pixels surrounded by the second pixels are aligned between the adjacent electrodes 112. This can align the centroid positions of the electrodes 112 for charge collection. For example, if the distances between the centroid positions of the adjacent electrodes 112 are not aligned, charges collected by each electrode may vary. More specifically, if the distance between a plurality of electrodes is longer than that between a plurality of other electrodes, charges that should be collected by a given electrode may be collected by another adjacent electrode. That is, the charge collection position in the semiconductor substrate 110 varies, causing deterioration in image quality. On the other hand, as shown in FIG. 2, by aligning the distances between the centroid positions of the adjacent electrodes 112, it is possible to prevent charges to be collected by a given electrode 112 from being collected by another electrode 112. That is, since it is possible to reduce variations in the charge collection position in the semiconductor substrate 110, it is possible to improve the image quality. The present invention is not limited to this, and for example, the electrodes 112a may be arranged at a pitch shorter than that of the electrodes 112b. The pitch at which the electrodes 112 are arranged can be defined as the distance between the geometric centroid positions of the adjacent electrodes 112 in orthogonal projection to the principal surface of the semiconductor substrate 110.

Referring to FIG. 2, the pixels of 7 columns×5 rows are arranged on the semiconductor substrate 110. However, the number of pixels is not limited to this. An appropriate number of pixels (electrodes 112) are arranged in accordance with the size of the semiconductor substrate 110 and the size of each electrode 112.

Figure 3:
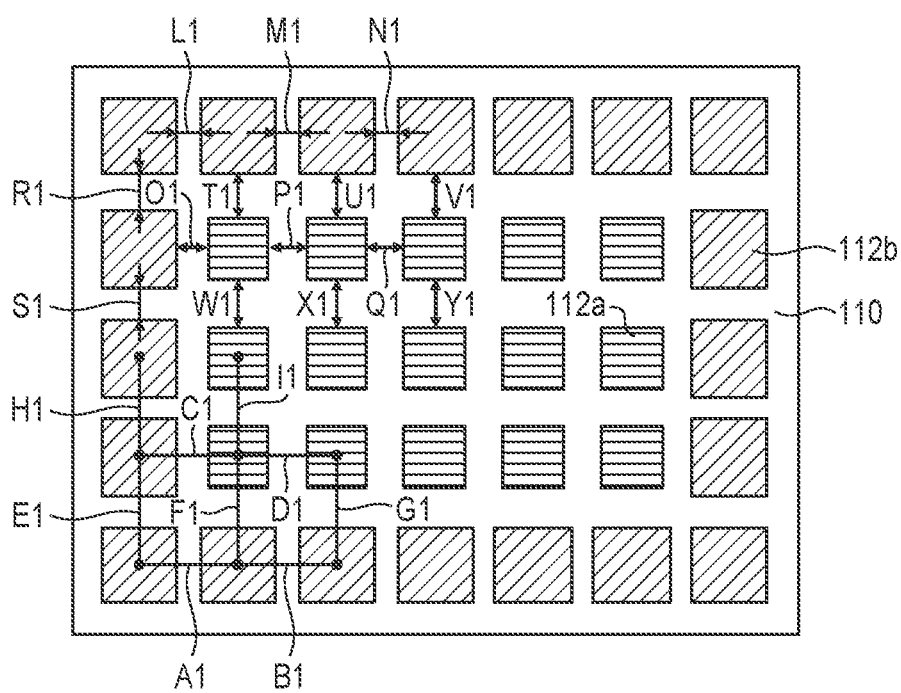
FIG. 3 is a view showing the example of the arrangement of the electrodes arranged on the semiconductor substrate of the radiation detector shown in FIG. 1.

FIG. 3 shows the length of each line connecting the centroid positions of the adjacent electrodes 112 and the interval between the adjacent electrodes 112 in the arrangement shown in FIG. 2. FIG. 3 shows lengths and intervals with respect to only some electrodes 112 but the same applies to the remaining regions based on the arrangement shown in FIG. 3. Each of lengths A1 to I1 represents the length of a line connecting the centroid positions of the adjacent electrodes 112. Each of intervals L1 to Y1 represents the interval between the adjacent electrodes 112. Each of the lengths A1 and B1 represents the length of a line connecting the centroid positions of the two adjacent electrodes 112b arranged on the same row. The length C1 represents the length of a line connecting the centroid positions of the two adjacent electrodes 112b and 112a arranged on the same row. The length D1 represents the length of a line connecting the centroid positions of the two adjacent electrodes 112a arranged on the same row. Each of the lengths E1 and H1 represents the length of a line connecting the centroid positions of the two adjacent electrodes 112b arranged on the same column. Each of the lengths F1 and G1 represents the length of a line connecting the centroid positions of the two adjacent electrodes 112b and 112a arranged on the same column. The length I1 represents the length of a line connecting the centroid positions of the two adjacent electrodes 112a arranged on the same column. The lengths A1 to I1 can have relationships of A1=B1=C1=D1 and E1=F1=G1=H1=I1, or may have relationships of A1=B1=C1=D1=E1=F1=G1=H1=I1. However, the relationship indicated by an equal sign (=) is not limited to a completely equal relationship and may be an almost equal relationship since a shift may occur due to a manufacturing error of the apparatus. By arranging the electrodes 112 by setting the intervals between the centroid positions of the adjacent electrodes 112 to be almost equal to each other, it is possible to reduce variations in the charge collection position in the semiconductor substrate 110.

Next, the intervals L1 to Y1 will be described. Each of the intervals L1, M1, and N1 represents the interval between the two adjacent electrodes 112b arranged on the same row. The interval O1 represents the interval between the two adjacent electrodes 112b and 112a arranged on the same row. Each of the intervals P1 and Q1 represents the interval between the two adjacent electrodes 112a arranged on the same row. Each of the intervals R1 and S1 represents the interval between the two adjacent electrodes 112b arranged on the same column. Each of the intervals T1, U1, and V1 represents the interval between the two adjacent electrodes 112b and 112a arranged on the same column. Each of the intervals W1, X1, and Y1 represents the interval between the two adjacent electrodes 112a arranged on the same column. The intervals L1 to Y1 can have relationships of P1=Q1>O1>L1=M1=N1 and R1=S1<T1=U1=V1<W1=X1=Y1. However, the relationship indicated by an equal sign (=) is not limited to a completely equal relationship and may be an almost equal relationship since a shift may occur due to a manufacturing error of the apparatus. That is, the interval between the adjacent electrodes having relatively large areas is set as the first interval. The second interval between the electrode having a relatively large area and the electrode having a small area which are adjacent to each other is larger than the first interval. Furthermore, the third interval between the adjacent electrodes having relatively small areas is larger than the second interval. If the plurality of electrodes 112 of different sizes are provided, they are laid out using the first to third intervals. This can reduce variations in the charge collection position in the semiconductor substrate 110.

Figure 4:
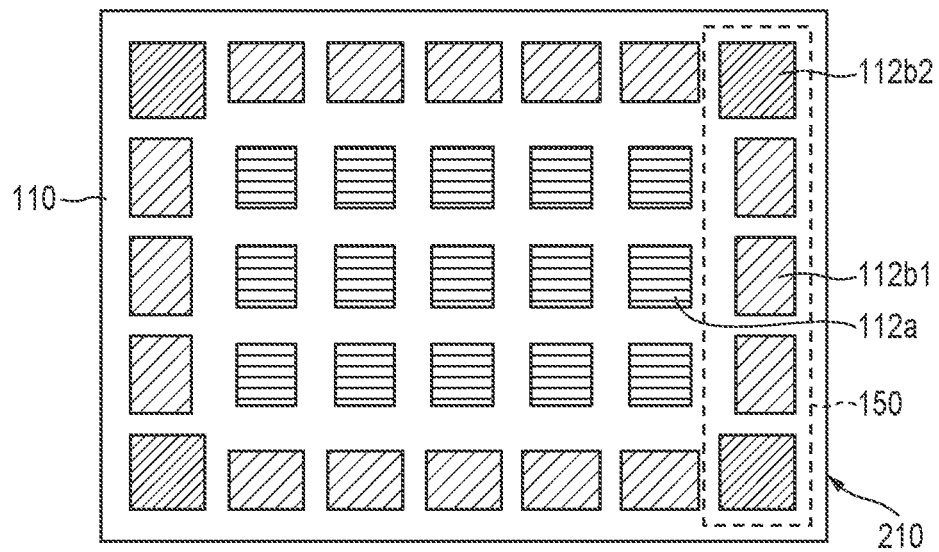
FIG. 4 is a view showing another example of the arrangement of the electrodes arranged on the semiconductor substrate of the radiation detector shown in FIG. 1.

FIG. 4 is a view showing a modification of the arrangement of the electrodes 112 shown in FIG. 2. In orthogonal projection to the principal surface of the semiconductor substrate 110 on which the electrodes 112 are arranged, the semiconductor substrate 110 has a rectangular shape. In the rectangular semiconductor substrate 110, the electric field between the electrodes 111 and 112 may be reduced and the charge collection efficiency may decrease at a corner, as compared with a side between the corners. To cope with this, the plurality of second pixels (electrodes 112b1 and 112b2 with oblique stripe patterns) arranged along the outer edge of the semiconductor substrate 110 include a plurality of third pixels (surrounded by a dotted line 150) arranged along one side (for example, a side 210) of the semiconductor substrate 110, and the area of the electrode 112b2 of the pixel arranged in an end portion among the plurality of third pixels may be larger than the area of the electrode 112b1 of the pixel which is not arranged in the end portion among the plurality of third pixels.

As shown in FIG. 4, the area of the electrode 112b2 of each of the two pixels arranged at the two ends among the pixels arranged along the side 210 may be larger than the area of the electrode 112b1 of each of the pixels other than the two pixels arranged at the two ends among the plurality of third pixels. As shown in FIG. 4, the electrode 112b2 arranged at each of four corners corresponding to the corners of the rectangular semiconductor substrate 110 may be larger than the electrodes 112b1 and 112a. However, the present invention is not limited to this, and the area of the electrode 112b2 of each of the two or more pixels arranged in the end portions among the plurality of third pixels arranged along one side may be larger than the area of each of the electrodes 112b1 and 112a of the remaining pixels. In accordance with the field strength at each of the positions of the plurality of second pixels (electrodes 112b1 and 112b2) arranged along the outer edge of the semiconductor substrate 110, the number of pixels in each of which the area of the electrode is made large in the end portion (corner) is decided.

Figure 5:
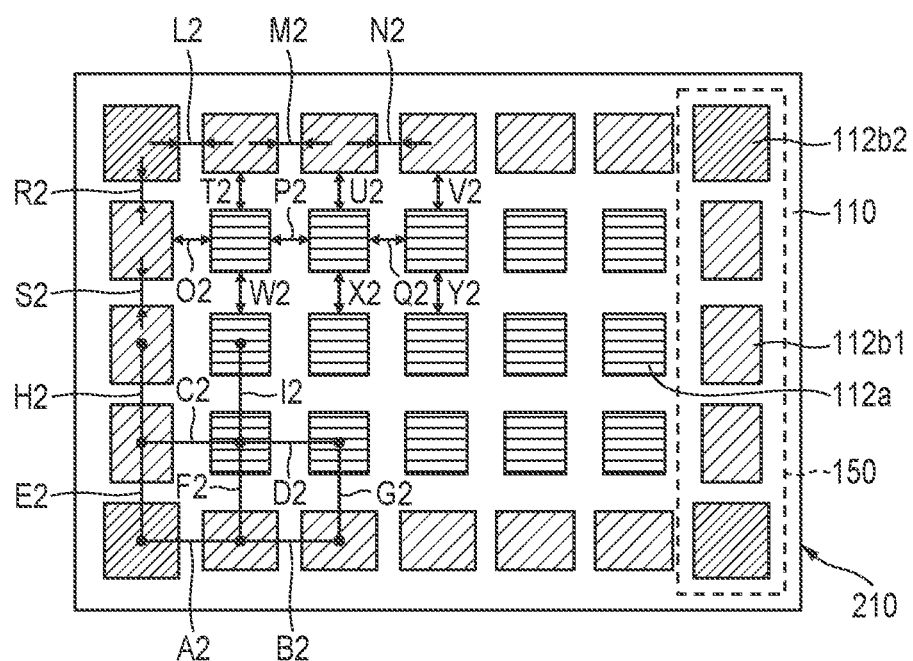
FIG. 5 is a view showing the other example of the arrangement of the electrodes arranged on the semiconductor substrate of the radiation detector shown in FIG. 1.

FIG. 5 is a view showing the modification of the arrangement of the electrodes 112 shown in FIG. 4. As described above, the distances between the centroid positions of the electrodes 112 may be aligned. With this arrangement, it is possible to implement uniform charge collection in the semiconductor substrate 110.

FIG. 5 shows the length of each line connecting the centroid positions of the adjacent electrodes 112 and the interval between the adjacent electrodes 112. FIG. 5 shows lengths and intervals with respect to only some electrodes 112 but the same applies to the remaining regions based on the arrangement shown in FIG. 5. Each of lengths A2 to I2 represents the length of a line connecting the centroid positions of the adjacent electrodes 112. Each of intervals L2 to Y2 represents the interval between the adjacent electrodes 112. The length A2 represents the length of a line connecting the centroid positions of the two adjacent electrodes 112$b$2 and 112$b$1 arranged on the same row. The length B2 represents the length of a line connecting the centroid positions of the two adjacent electrodes 112$b$1 arranged on the same row. The length C2 represents the length of a line connecting the centroid positions of the two adjacent electrodes 112$b$1 and 112$a$ arranged on the same row. The length D2 represents the length of a line connecting the centroid positions of the two adjacent electrodes 112$a$ arranged on the same row. The length E2 represents the length of a line connecting the centroid positions of the two adjacent electrodes 112$b$2 and 112$b$1 arranged on the same column. Each of the lengths F2 and G2 represents the length of a line connecting the centroid positions of the two adjacent electrodes 112$b$1 and 112$a$ arranged on the same column. The length H2 represents the length of a line connecting the centroid positions of the two adjacent electrodes 112$b$2 arranged on the same column. The length I2 represents the length of a line connecting the centroid positions of the two adjacent electrodes 112$a$ arranged on the same column. The lengths A2 to I2 can have relationships of A2=B2=C2=D2 and E2=F2=G2=H2=I2, or may have relationships of A2=B2=C2=D2=E2=F2=G2=H2=I2. However, the relationship indicated by an equal sign (=) is not limited to a completely equal relationship and may be an almost equal relationship since a shift may occur due to a manufacturing error of the apparatus. By arranging the electrodes 112 by setting the intervals between the centroid positions of the adjacent electrodes 112 to be almost equal to each other, it is possible to reduce variations in the charge collection position in the semiconductor substrate 110.

Next, the intervals L2 to Y2 will be described. The interval L2 represents the interval between the two adjacent electrodes 112$b$2 and 112$b$1 arranged on the same row. Each of the intervals M2 and N2 represents the interval between the two adjacent electrodes 112$b$1 arranged on the same row. The interval O2 represents the interval between the two adjacent electrodes 112$b$1 and 112$a$ arranged on the same row. Each of the intervals P2 and Q2 represents the interval between the two adjacent electrodes 112$a$ arranged on the same row. The interval R2 represents the interval between the two adjacent electrodes 112$b$2 and 112$b$1 arranged on the same column. The interval S2 represents the interval between the two adjacent electrodes 112$b$1 arranged on the same column. Each of the intervals T2, U2, and V2 represents the interval between the two adjacent electrodes 112$b$1 and 112$a$ arranged on the same column. Each of the intervals W2, X2, and Y2 represents the interval between the two adjacent electrodes 112$a$ arranged on the same column. The intervals L2 to Q2 can have relationships of P2=Q2>M2=N2>L2 and O2>M2. The intervals O2 and P2 can have one of relationships of O2>P2, O2<P2, and O2=P2 but may be set appropriately in accordance with the length of the width of the electrode 112$b$1 in the horizontal line. For example, the intervals O2 and P2 are set to satisfy a relationship of C2=D2. The intervals R2 to Y2 can have relationships of T2=U2=V2 and W2=X2=Y2>S2>R2. The intervals V2 and W2 can have one of relationships of V2>W2, V2<W2, and V2=W2 but may be set appropriately in accordance with the length of the electrode 112$b$1 in the vertical direction. For example, the intervals V2 and W2 are set to satisfy a relationship of F2=I2. However, the relationship indicated by an equal sign (=) is not limited to a completely equal relationship and may be an almost equal relationship since a shift may occur due to a manufacturing error of the apparatus. That is, the interval between the adjacent electrodes having relatively large areas is set as the first interval. The second interval between the electrode having a relatively large area and the electrode having an intermediate area which are adjacent to each other is larger than the first interval. The second interval between the electrode having a relatively intermediate area and the electrode having an intermediate area which are adjacent to each other is larger than the first interval. Furthermore, the third interval between the adjacent electrodes having relatively small areas is larger than the second interval. If the plurality of electrodes 112 of different sizes are provided, they are laid out using the first to third intervals. This can reduce variations in the charge collection position in the semiconductor substrate 110.

Figure 6:
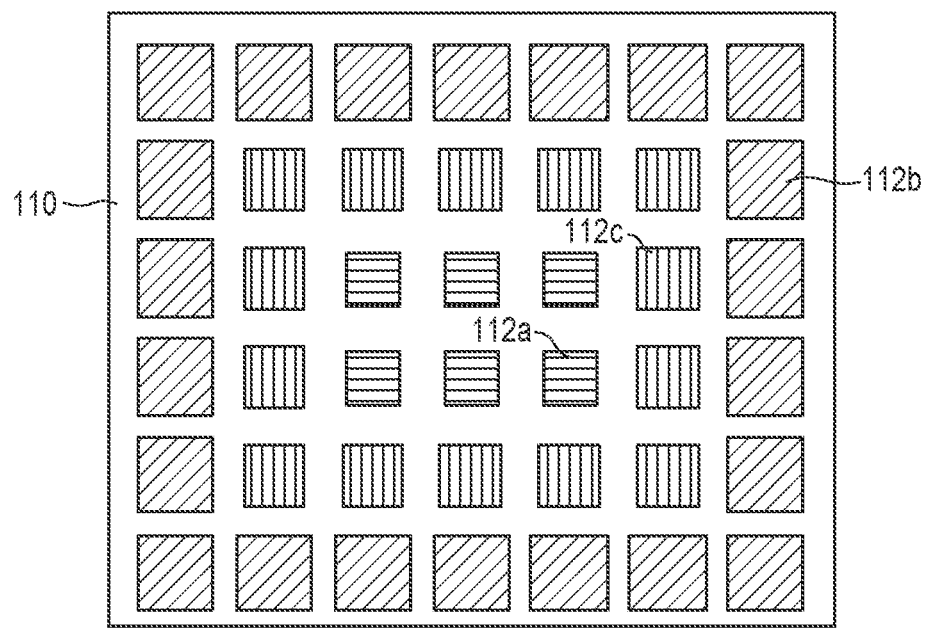
FIG. 6 is a view showing still another example of the arrangement of the electrodes arranged on the semiconductor substrate of the radiation detector shown in FIG. 1.

FIG. 6 is a view showing a modification of the arrangement of the electrodes 112 shown in FIG. 2. FIG. 6 does not illustrate the distances between the centroid positions of the electrodes 112 but the distances between the centroid positions of the electrodes 112 are almost equal to each other in FIG. 6. With respect to the intervals between the electrodes 112, the interval between the electrode 112$a$ and an electrode 112$c$ which are adjacent to each other is larger than the interval between the adjacent electrodes 112$b$ and 112$c$. FIG. 2 shows the example in which the electrodes 112 of the two kinds of sizes are arranged such that the area of each of the electrodes 112$b$ arranged on the outermost periphery of the semiconductor substrate 110 is larger than the area of each of the electrodes 112$a$ surrounded by the electrodes 112$b$. However, the influence of the reduction in the electric field between the electrodes 111 and 112 in the end portion of the semiconductor substrate 110 may appear over several rounds such as two or three rounds from the outermost periphery. The plurality of pixels arranged on the semiconductor substrate 110 may include a plurality of fourth pixels (electrodes 112$c$ with a vertical stripe pattern) arranged between the plurality of first pixels (electrodes 112$a$ with the horizontal stripe pattern) and the plurality of second pixels (electrodes 112$b$ with the oblique stripe pattern), and the area of the electrode 112$c$ of each of the plurality of fourth pixels may be larger than the area of the electrode 112$a$ of each of the plurality of first pixels and equal to or smaller than the area of the electrode 112$b$ of each of the plurality of second pixels. In the arrangement shown in FIG. 6, the area of the electrode 112$c$ is smaller than the area of the electrode 112$b$ but the area of the electrode 112$c$ may be equal to the area of the electrode 112$b$ in accordance with the field strength of the fourth pixel (electrode 112$c$). In the arrangement shown in FIG. 6, the electrodes 112$c$ are arranged in only one row (one round) but may be arranged in two or more rows (two or more rounds). The number of rows (rounds) of the pixels in each of which the electrode 112$c$ is arranged is decided in accordance with the field strength at the position of each of the plurality of pixels arranged on the semiconductor substrate 110.

In the above description, to compensate the decrease in the charge collection efficiency in the pixels arranged along the outer edge of the semiconductor substrate 110, the area of the electrode 112b of each of the pixels arranged along the outer edge of the semiconductor substrate 110 is made larger than the area of the electrode 112a of each of the remaining pixels. However, the method of making the output sensitivity of each of the pixels arranged in the outer edge portion of the semiconductor substrate 110 higher than the output sensitivity of each of the remaining pixels surrounded by the pixels arranged in the outer edge portion is not limited to this. For example, the radiation detector 100 may further include an amplifier that amplifies signals corresponding to the charges generated by the plurality of pixels. In this case, an amplification factor with which signals output from the plurality of second pixels arranged along the outer edge of the semiconductor substrate 110 are amplified is larger than an amplification factor with which signals output from the plurality of first pixels surrounded by the plurality of second pixels are amplified. The change of the area according to the arrangement position of each electrode 112 and the change of the amplification factor by the amplifier may be combined.

An amplifier may be arranged in the integrated circuit 130, for example, in correspondence with each pixel. For example, a column circuit corresponding to each pixel column of the plurality of pixels arranged on the semiconductor substrate 110 may be arranged in the integrated circuit 130, and an amplifier may be arranged in each column circuit. For example, a circuit board including an amplifier may be arranged in the radiation detector 100 separately from the integrated circuit 130.

With respect to the change of the area of each electrode 112, the size can freely be designed in accordance with the position of the semiconductor substrate 110. In other words, it is possible to cope with an increase/decrease of one charge. On the other hand, with respect to amplification by the amplifier, for example, the degree of freedom of amplification may be low, for example, an integer multiple such as twice or four times is used. Therefore, considering tonality and the like, the degree of freedom of design of the radiation detector 100 can be improved by changing the area of each electrode 112, and it is possible to more effectively suppress the influence of deterioration in image quality caused by the decrease in the charge collection efficiency.

In the above description, by making the output sensitivity of each of the pixels arranged in the outer edge portion of the semiconductor substrate 110 higher than the output sensitivity of each of the remaining pixels surrounded by the pixels arranged in the outer edge portion, the decrease in the charge collection efficiency in the pixels arranged in the outer edge portion of the semiconductor substrate 110 is compensated. The method of compensating the decrease in the charge collection efficiency in the pixels arranged in the outer edge portion of the semiconductor substrate 110 is not limited to this.

Figure 7:
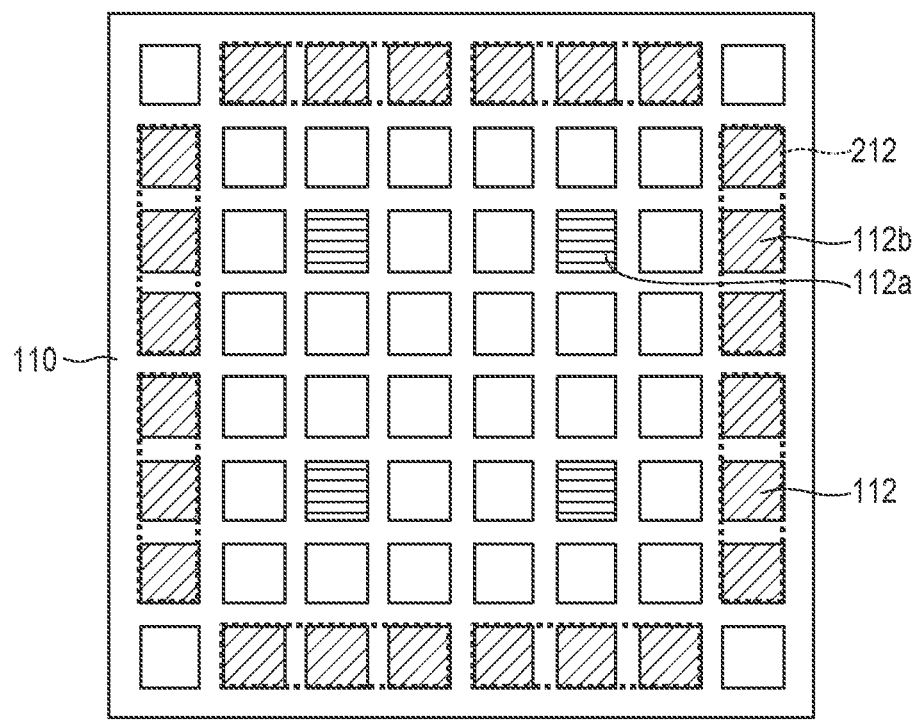
FIG. 7 is a view showing still another example of the arrangement of the electrodes arranged on the semiconductor substrate of the radiation detector shown in FIG. 1.

FIG. 7 is a view showing an example of the arrangement of the electrodes 112 arranged on the semiconductor substrate 110. Consider a case in which signals are read out from some of the plurality of pixels whose positions are respectively defined by the electrodes 112. For example, consider a case in which signals are read out from the remaining pixels obtained by thinning out some pixels instead of reading out signals from all the pixels, such as a high-speed readout operation. In FIG. 7, signals are read out from the pixels in each of which the electrode 112 is indicated by a stripe pattern.

As in the above description, the plurality of pixels include the plurality of first pixels whose positions are defined by the electrodes 112a and the plurality of second pixels whose positions are defined by the electrodes 112b arranged along the outer edge of the semiconductor substrate 110 to surround the plurality of first pixels. In the arrangement shown in FIG. 7, the area of the electrode 112a of each of the plurality of first pixels is equal to the area of the electrode 112b of each of the plurality of second pixels.

In this embodiment, the signals of the plurality of first pixels are output as the first signal based on the signal values of signals output from one or more pixels (the electrodes 112a with a horizontal stripe pattern in FIG. 7) among the plurality of first pixels, and the signals of the plurality of second pixels are output as the second signal based on the signal values of signals output from two or more pixels (the electrodes 112b with an oblique stripe pattern in FIG. 7) among the plurality of second pixels. In this case, the number of pixels used to generate the second signal among the plurality of second pixels is larger than the number of pixels used to generate the first signal among the plurality of first pixels. In the arrangement shown in FIG. 7, the first signal is generated based on a signal output from one first pixel. On the other hand, in the arrangement shown in FIG. 7, the second signal is generated by adding the signal values of signals output from three pixels, among the plurality of second pixels, which are arranged adjacent to each other and in which the outer edges of the electrodes 112b are connected by a virtual line 212. This can suppress the decrease in the charge collection efficiency in the pixels arranged in the outer edge portion of the semiconductor substrate 110.

The number of first pixels used to generate the first signal and the number of second pixels used to generate the second signal are not limited to the above example, and can be set appropriately. When the number of pixels used to generate the second signal among the plurality of second pixels is larger than the number of pixels used to generate the first signal among the plurality of first pixels, the above-described effect is obtained and deterioration in image quality of the radiation image is suppressed.

Figure 8:
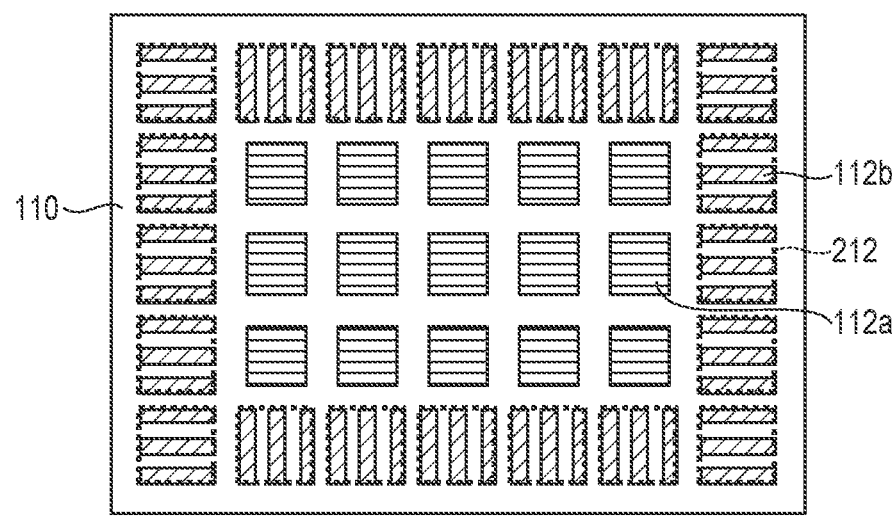
FIG. 8 is a view showing still another example of the arrangement of the electrodes arranged on the semiconductor substrate of the radiation detector shown in FIG. 1.

FIG. 8 is a view for explaining a signal readout method when the area of the electrode 112a (horizontal stripe pattern) of each of the plurality of first pixels is larger than the area of the electrode 112b (oblique stripe pattern) of each of the plurality of second pixels arranged along the outer edge of the semiconductor substrate 110. That is, this signal readout method is a method when the relationship between the sizes of the electrodes 112a and 112b is reversed, as compared with FIGS. 2 to 6. The arrangement of the electrodes 112 shown in FIG. 8 assumes that signals are read out from all the pixels.

In this case as well, similar to the case shown in FIG. 7, the signals of the plurality of first pixels are output as the first signal based on the signal values of signals output from one or more pixels among the plurality of first pixels, and the signals of the plurality of second pixels are output as the second signal based on the signal values of signals output from two or more pixels among the plurality of second pixels. In this case, the number of pixels used to generate the second signal among the plurality of second pixels is larger than the number of pixels used to generate the first signal among the plurality of first pixels. In the arrangement shown in FIG. 8, the first signal is generated based on a signal output from one first pixel. On the other hand, in the arrangement shown in FIG. 8, the second signal is generated by adding the signal values of signals output from three pixels, among the plurality of second pixels, which are arranged adjacent to each other and in which the outer edges of the electrodes 112b are connected by the virtual line 212. This can suppress the decrease in the charge collection efficiency in the pixels arranged in the outer edge portion of the semiconductor substrate 110.

As the area of the electrode 112b is larger, the traveling distance of charges through the electrode 112b is longer, and thus the time taken to read out charges is longer. Therefore, for example, if the readout time is shorter, generated charges may not be read out, thereby decreasing the charge collection efficiency. To cope with this, in this embodiment, the electrode 112b of each of the pixels arranged along the outer edge of the semiconductor substrate 110 is made smaller than the electrode 112a, and the second signal is generated by adding the signal values of the signals output from the plurality of second pixels. This can suppress the decrease in the charge collection efficiency in the pixels arranged in the outer edge portion of the semiconductor substrate 110, and suppress deterioration in image quality of the radiation image.

The plurality of second pixels for generating one second signal are arranged adjacent to each other, as shown in FIG. 8. In this case, the area of a region surrounded by the virtual line 212 connecting the outer edges of the electrodes 112b of the plurality of second pixels for generating one second signal may be larger than the area of the electrode 112a of each of the plurality of first pixels. In this example, the centroid of the region surrounded by the virtual line 212 connecting the outer edges of the plurality of electrodes 112b included in the plurality of second pixels for generating one second signal can be said as the centroid of the "electrodes" included in the plurality of second pixels for generating one second signal. If the interval between the electrodes of the plurality of adjacent pixels is considered, this can be regarded as the interval from the end portion of the region surrounded by the virtual line 212 to the electrode of another pixel or the end portion of the region surrounded by the virtual line 212 in other pixels. That is, by combining regions influenced by an electric field generated by the plurality of small electrodes 112b, it is possible to obtain the region equal to a region influenced by an electric field generated by an electrode (for example, the electrode 112b shown in FIG. 2) having an area larger than the area of the electrode 112a.

Figure 9:
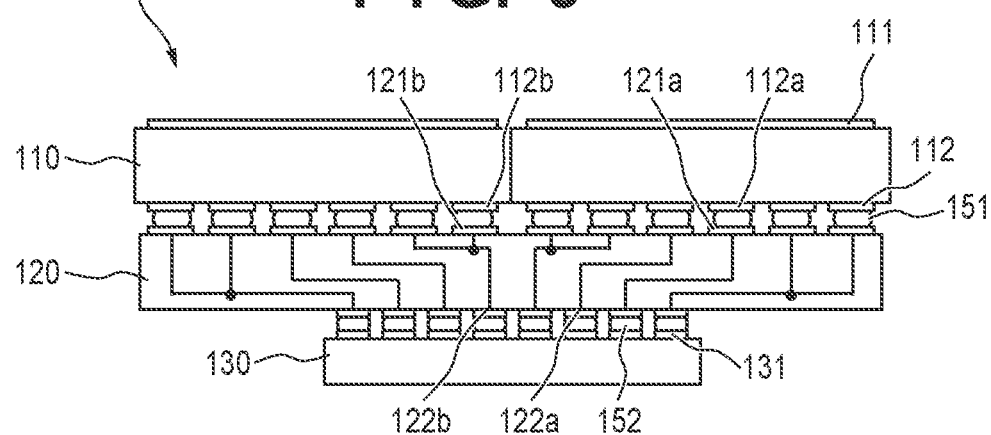
FIG. 9 is a view showing an example of the arrangement of an interposer of the radiation detector shown in FIG. 1.

A method of generating one signal by adding the signal values of a plurality of signals, as shown in FIGS. 7 and 8, will be described next. As described above, the interposer 120 including the plurality of terminals 121 (input terminals) electrically connected to the electrodes 112 of the plurality of pixels is arranged to face the semiconductor substrate 110. In this case, as shown in FIG. 9, the plurality of terminals 121 include a plurality of first input terminals 121a connected to the electrodes 112a of the plurality of first pixels and a plurality of second input terminals 121b connected to the electrodes 112b of the plurality of second pixels. Furthermore, the interposer 120 includes a first output terminal 122a that is connected to one or more of the plurality of first input terminals 121a and outputs the first signal, and a second output terminal 122b that is connected to two or more of the plurality of second input terminals 121b and outputs the second signal. In this case, the number of input terminals connected to the second output terminal 122b among the plurality of second input terminals 121b may be larger than the number of input terminals connected to the first output terminal 122b among the plurality of first input terminals 121a.

In the arrangement shown in FIG. 9, in the interposer 120, a signal input from one input terminal 121a is directly output from the output terminal 122a. On the other hand, the signal values of signals input from two input terminals 121b are combined in the interposer 120, and output from one output terminal 122b. The present invention, however, is not limited to this, and the number of input terminals 121a connected to one output terminal 122a and the number of input terminals 121b connected to one output terminal 122b are set appropriately.

Figure 10:
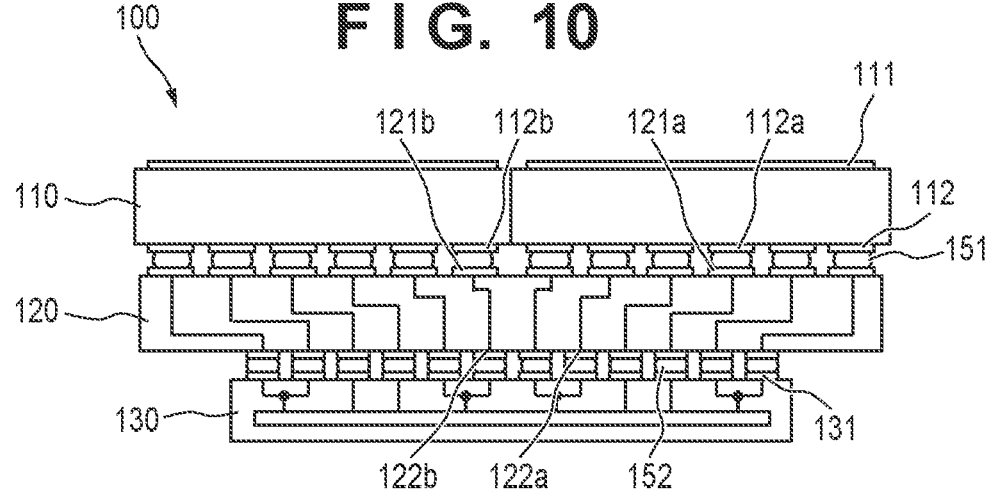
FIG. 10 is a view showing an example of the operation of an integrated circuit of the radiation detector shown in FIG. 1.

For example, as in an arrangement shown in FIG. 10, the integrated circuit 130 may output the first signal based on the signal values of signals output from one or more of the plurality of first pixels, and output the second signal based on the signal values of signals output from two or more of the plurality of second pixels. In this case as well, the number of pixels used to generate the second signal among the plurality of second pixels is larger than the number of pixels used to generate the first signal among the plurality of first pixels. In this case, in the interposer 120, one input terminal 121a or 121b is connected to one output terminal 122a or 122b.

Figure 11A:
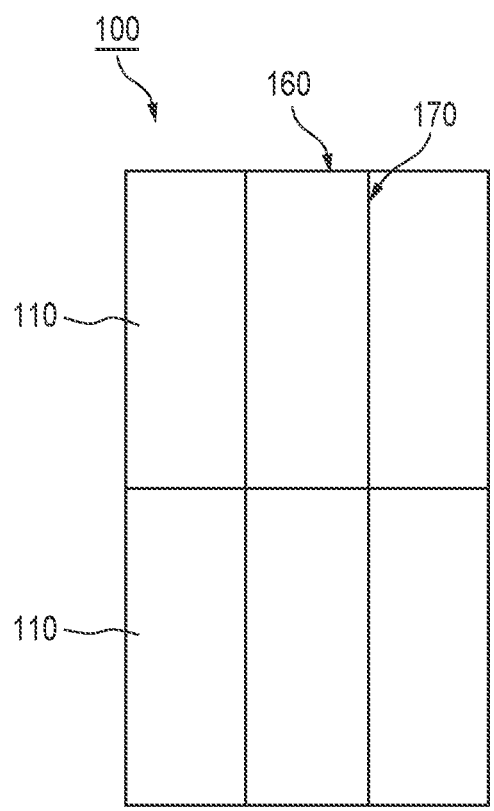
FIGS. 11A and 11B are views showing an example of the arrangement of semiconductor substrates in the radiation detector shown in FIG. 1.
Figure 11B:
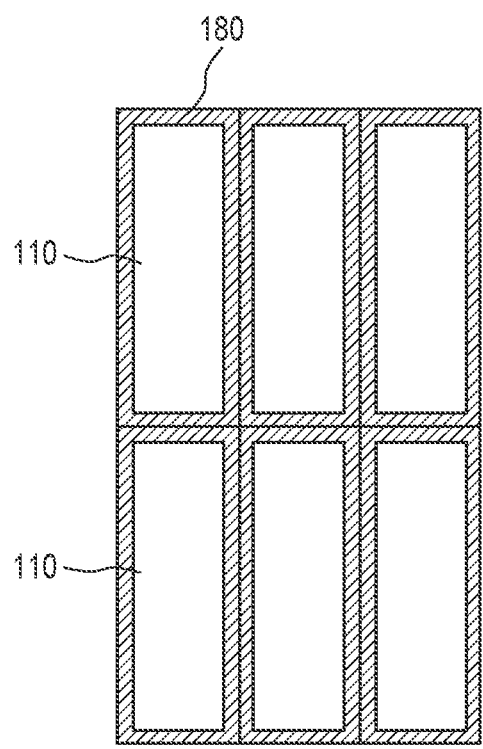

As shown in FIG. 11A, in the radiation detector 100, the semiconductor substrates 110 each including the plurality of pixels, as described above, can be tiled. If the semiconductor substrate 110 includes no pixels, the charge collection efficiency in the pixels arranged in the outer edge portion of the semiconductor substrate 110 is low, and thus a sensitivity reduction region 180 may be generated at the boundary between the semiconductor substrates 110, as shown in FIG. 11B, thereby degrading image quality. On the other hand, in this embodiment, the decrease in the charge collection efficiency in the pixels arranged in the outer edge portion of the semiconductor substrate 110 is suppressed, thereby suppressing generation of the sensitivity reduction region 180. This can suppress deterioration in image quality of the radiation image obtained by the radiation detector 100.

In a portion 170 shown in FIG. 11A where the semiconductor substrates 110 are adjacent to each other, the reduction in the electric field generated by the electrodes 111 and 112 may be reduced, as compared with a portion 160 of the semiconductor substrate 110 forming the outer edge of the radiation detector 100. Therefore, for example, the area of the electrode 112 of each of the pixels arranged along the portion 160, of the outer edge of the semiconductor substrate 110, forming the outer edge of the radiation detector 100 may be larger than the area of the electrode 112 of each of the pixels arranged along the portion 170 of the outer edge of the semiconductor substrate 110, where the semiconductor substrates 110 are adjacent to each other. For example, an amplification factor with which signals output from the pixels arranged along the portion 160, of the outer edge of the semiconductor substrate 110, forming the outer edge of the radiation detector 100 are amplified may be larger than an amplification factor with which signals output from the pixels arranged along the portion 170 of the outer edge of the semiconductor substrate 110, where the semiconductor substrates 110 are adjacent to each other, are amplified. Furthermore, for example, the signals of the pixels arranged along the portion 160, of the outer edge of the semiconductor substrate 110, forming the outer edge of the radiation detector 100 are output as the third signal based on the signal values of signals output from two or more pixels, the signals of the pixels arranged along the portion 170 of the outer edge of the semiconductor substrate 110, where the semiconductor substrates 110 are adjacent to each other, are output as the fourth signal based on the signal values of signals output from two or more pixels, and the number of pixels used to generate the third signal may be larger than the number of pixels used to generate the fourth signal.

Figure 12:
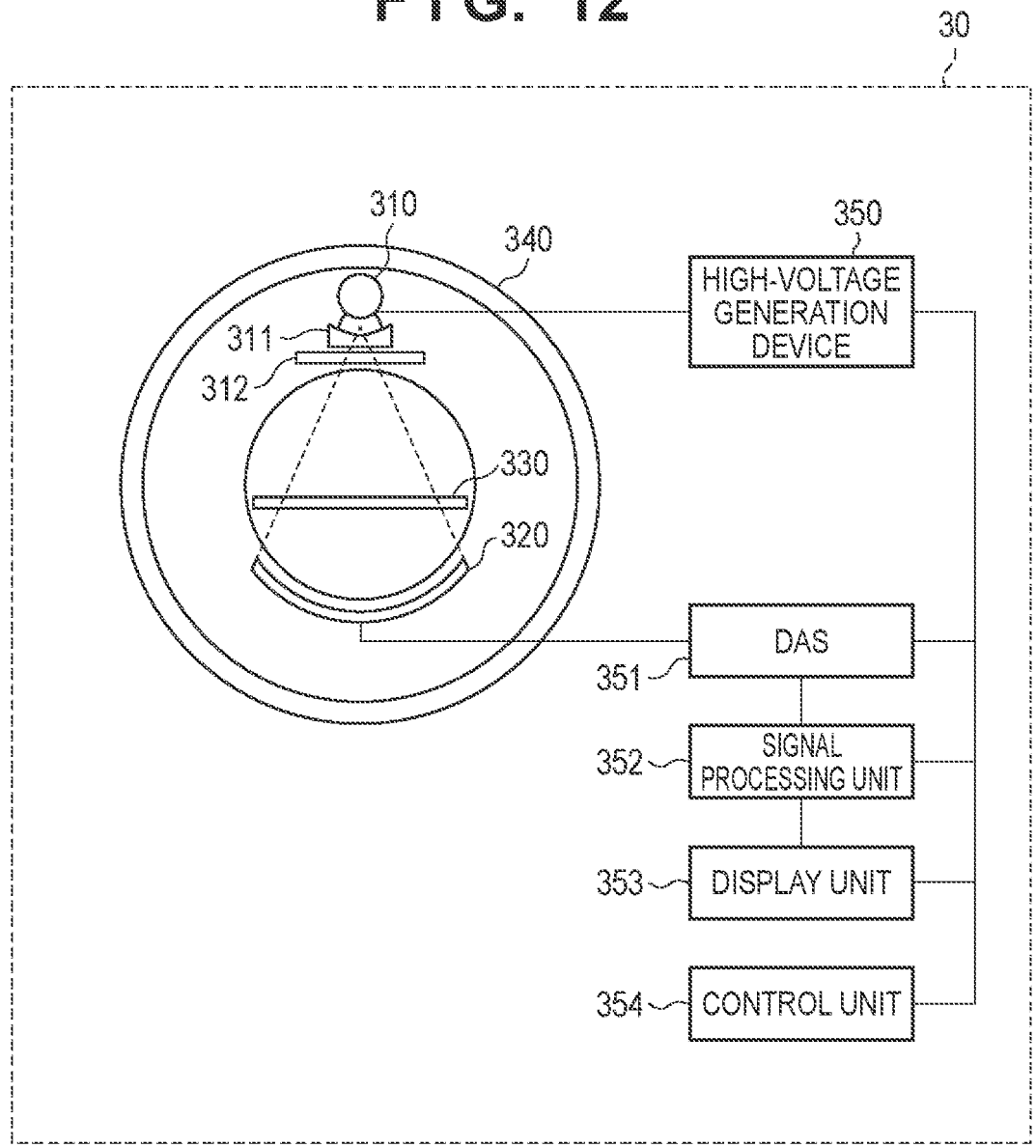
FIG. 12 is a view showing an example of the arrangement of a radiation CT apparatus using the radiation detector shown in FIG. 1.

FIG. 12 is a block diagram of a radiation CT apparatus according to this embodiment. The above-described radiation detector 100 is applicable to a detector of the radiation CT apparatus. A radiation CT apparatus 30 according to this embodiment includes a radiation generation unit 310, a wedge 311, a collimator 312, a radiation detection unit 320, a top plate 330, a rotating frame 340, a high-voltage generation device 350, a DAS (data acquisition system) 351, a signal processing unit 352, a display unit 353, and a control unit 354.

The radiation generation unit 310 is formed from, for example, a vacuum tube that generates X-rays. The vacuum tube of the radiation generation unit 310 is supplied with a filament current and a high voltage from the high-voltage generation device 350. When thermoelectrons are emitted from a cathode (filament) to an anode (target), X-rays are generated.

The wedge 311 is a filter that adjusts the amount of radiation emitted from the radiation generation unit 310. The wedge 311 attenuates the amount of radiation so that the radiation emitted from the radiation generation unit 310 to an object has a predetermined distribution. The collimator 312 is formed from a lead plate that narrows the irradiation range of the radiation having passed through the wedge 311. The radiation generated by the radiation generation unit 310 is formed in a cone beam shape via the collimator 312, and the object on the top plate 330 is irradiated with the radiation.

The radiation detection unit 320 is formed using the above-described radiation detector 100. The radiation detection unit 320 detects the radiation having passed through the object from the radiation generation unit 310, and outputs a signal corresponding to the amount of the radiation to the DAS 351.

The rotating frame 340 is annular, and is configured to be rotatable. The radiation generation unit 310 (the wedge 311 and the collimator 312) and the radiation detection unit 320 are arranged to face each other in the rotating frame 340. The radiation generation unit 310 and the radiation detection unit 320 can rotate together with the rotating frame 340.

The high-voltage generation device 350 includes a boosting circuit, and outputs a high voltage to the radiation generation unit 310. The DAS 351 includes an amplification circuit and an A/D conversion circuit, and outputs, as digital data, a signal from the radiation detection unit 320 to the signal processing unit 352.

The signal processing unit 352 includes a CPU (Central Processing Unit), a ROM (Read Only Memory), and a RAM (Random Access Memory), and can execute image processing and the like for the digital data. The display unit 353 includes a flat display device, and can display a radiation image. The control unit 354 includes a CPU, a ROM, and a RAM, and controls the operation of the overall radiation CT apparatus 30.

According to the present invention, there can be provided a technique advantageous in suppressing a decrease in charge collection efficiency in the end portion of the semiconductor substrate.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2023-034933, filed Mar. 7, 2023, which is hereby incorporated by reference herein in its entirety.

What is claimed is:

1. A radiation detector obtained by arranging a plurality of pixels on a semiconductor substrate configured to convert incident radiation into charges, wherein
   the plurality of pixels comprise a plurality of first pixels, and a plurality of second pixels arranged along an outer edge of the semiconductor substrate,
   each of the plurality of second pixels has output sensitivity higher than output sensitivity of each of the plurality of first pixels, and
   an interval between adjacent second pixels among the plurality of second pixels is smaller than an interval between adjacent first pixels among the plurality of first pixels.

2. The detector according to claim 1, wherein
   each of the plurality of pixels comprises an electrode arranged on one principal surface out of two principal surfaces of the semiconductor substrate, and
   an area of the electrode of each of the plurality of second pixels is larger than an area of the electrode of each of the plurality of first pixels.

3. The detector according to claim 2, wherein
   in orthogonal projection to the principal surface, the semiconductor substrate has a rectangular shape,
   the plurality of second pixels comprise a plurality of third pixels arranged along one side of the semiconductor substrate, and
   an area of the electrode of a pixel, which is arranged in an end portion, among the plurality of third pixels is larger than an area of the electrode of a pixel, which is not arranged in the end portion, among the plurality of third pixels.

4. The detector according to claim 3, wherein an area of the electrode of each of two pixels arranged at two ends among the plurality of third pixels is larger than an area of the electrode of each of pixels other than the two pixels among the plurality of third pixels.

5. The detector according to claim 2, wherein
   the plurality of pixels comprise a plurality of fourth pixels arranged between the plurality of first pixels and the plurality of second pixels, and
   an area of the electrode of each of the plurality of fourth pixels is larger than the area of the electrode of each of the plurality of first pixels and is not larger than the area of the electrode of each of the plurality of second pixels.

6. The detector according to claim 1, further comprising an amplifier configured to amplify signals corresponding to charges generated by the plurality of pixels,
   wherein an amplification factor with which signals output from the plurality of second pixels are amplified is larger than an amplification factor with which signals output from the plurality of first pixels are amplified.

7. The detector according to claim 1, wherein the plurality of second pixels are pixels arranged at positions closest to the outer edge of the semiconductor substrate among the plurality of pixels.

8. The detector according to claim 1, wherein the plurality of second pixels are arranged along the outer edge of the semiconductor substrate to surround the plurality of first pixels.

9. The detector according to claim 1, wherein a plurality of semiconductor substrates are tiled.

10. The detector according to claim 1, wherein the semiconductor substrate is a single crystal substrate made of cadmium zinc telluride.

11. The detector according to claim 1, wherein the semiconductor substrate is a single crystal substrate made of one of cadmium telluride, lead iodide, mercury iodide, bismuth iodide, and thallium bromide.

12. A radiation CT apparatus comprising:
the radiation detector according to claim 1;
a radiation generator configured to irradiate the radiation detector with radiation; and
a signal processor configured to process a signal output from the radiation detector.

13. A radiation detector obtained by arranging a plurality of pixels on a semiconductor substrate configured to convert incident radiation into charges, wherein
the plurality of pixels comprise a plurality of first pixels, and a plurality of second pixels arranged along an outer edge of the semiconductor substrate,
each of the plurality of pixels comprises an electrode arranged on one principal surface out of two principal surfaces of the semiconductor substrate,
an area of the electrode of each of the plurality of second pixels is larger than an area of the electrode of each of the plurality of first pixels, and
an interval between adjacent electrodes among the electrodes of the plurality of second pixels is smaller than an interval between adjacent electrodes among the electrodes of the plurality of first pixels.

14. The detector according to claim 13, wherein a length of a line connecting centroid positions of the electrodes of two adjacent second pixels among the plurality of second pixels is equal to a length of a line connecting centroid positions of the electrodes of two adjacent first pixels among the plurality of first pixels.

15. The detector according to claim 14, wherein one second pixel among the plurality of second pixels and one first pixel among the plurality of first pixels are adjacent to each other, and a length of a line connecting centroid positions of the electrodes of the one second pixel and the one first pixel is equal to a length of a line connecting centroid positions of the electrodes of two adjacent second pixels among the plurality of second pixels.

16. The detector according to claim 13, wherein one second pixel among the plurality of second pixels and one first pixel among the plurality of first pixels are adjacent to each other, and an interval between the electrode of the one second pixel and the electrode of the one first pixel is smaller than the interval between adjacent electrodes among the electrodes of the plurality of second pixels.

17. The detector according to claim 13, wherein
in orthogonal projection to the principal surface, the semiconductor substrate has a rectangular shape,
the plurality of second pixels comprise a plurality of third pixels arranged along one side of the semiconductor substrate, and
an area of the electrode of a pixel, which is arranged in an end portion, among the plurality of third pixels is larger than an area of the electrode of a pixel, which is not arranged in the end portion, among the plurality of third pixels.

18. The detector according to claim 17, wherein an area of the electrode of each of two pixels arranged at two ends among the plurality of third pixels is larger than an area of the electrode of each of pixels other than the two pixels among the plurality of third pixels.

19. The detector according to claim 13, wherein
the plurality of pixels comprise a plurality of fourth pixels arranged between the plurality of first pixels and the plurality of second pixels, and
an area of the electrode of each of the plurality of fourth pixels is larger than the area of the electrode of each of the plurality of first pixels and is not larger than the area of the electrode of each of the plurality of second pixels.

20. The detector according to claim 13, further comprising an amplifier configured to amplify signals corresponding to charges generated by the plurality of pixels,
wherein an amplification factor with which signals output from the plurality of second pixels are amplified is larger than an amplification factor with which signals output from the plurality of first pixels are amplified.

21. The detector according to claim 13, wherein a plurality of semiconductor substrates are tiled.

22. The detector according to claim 13, wherein the semiconductor substrate is a single crystal substrate made of cadmium zinc telluride.

23. The detector according to claim 13, wherein the semiconductor substrate is a single crystal substrate made of one of cadmium telluride, lead iodide, mercury iodide, bismuth iodide, and thallium bromide.

24. A radiation CT apparatus comprising:
the radiation detector according to claim 13;
a radiation generator configured to irradiate the radiation detector with radiation; and
a signal processor configured to process a signal output from the radiation detector.

25. A radiation detector obtained by arranging a plurality of pixels on a semiconductor substrate configured to convert incident radiation into charges, wherein
the plurality of pixels comprise a plurality of first pixels, and a plurality of second pixels arranged along an outer edge of the semiconductor substrate,
signals of the plurality of first pixels are output as a first signal based on a signal value of a signal output from at least one pixel among the plurality of first pixels,
signals of the plurality of second pixels are output as a second signal based on signal values of signals output from at least two pixels among the plurality of second pixels, and
the number of pixels used to generate the second signal among the plurality of second pixels is larger than the number of pixels used to generate the first signal among the plurality of first pixels.

26. The detector according to claim 25, wherein
each of the plurality of pixels comprises an electrode arranged on one principal surface out of two principal surfaces of the semiconductor substrate, and
an area of the electrode of each of the plurality of first pixels is equal to an area of the electrode of each of the plurality of second pixels.

27. The detector according to claim 25, wherein
each of the plurality of pixels comprises an electrode arranged on one principal surface out of two principal surfaces of the semiconductor substrate, and
an area of the electrode of each of the plurality of first pixels is larger than an area of the electrode of each of the plurality of second pixels.

28. The detector according to claim 27, wherein
the second signal is generated from signal values of signals output from a plurality of fifth pixels arranged adjacent to each other among the plurality of second pixels, and an area of a region surrounded by a virtual line connecting outer edges of the electrodes of the plurality of fifth pixels is larger than the area of the electrode of each of the plurality of first pixels.

29. The detector according to claim 26, further comprising an interposer facing the semiconductor substrate and comprising a plurality of input terminals electrically connected to the electrodes of the plurality of pixels, wherein the plurality of input terminals comprise a plurality of first input terminals connected to the electrodes of the plurality of first pixels, and a plurality of second input terminals connected to the electrodes of the plurality of second pixels, the interposer further comprises a first output terminal connected to at least one input terminal among the plurality of first input terminals and configured to output the first signal, and a second output terminal connected to at least two input terminals among the plurality of second input terminals and configured to output the second signal, and the number of input terminals connected to the second output terminal among the plurality of second input terminals is larger than the number of input terminals connected to the first output terminal among the plurality of first input terminals.

30. The detector according to claim 25, further comprising an integrated circuit configured to process signals output from the plurality of pixels, wherein the integrated circuit outputs the first signal based on a signal value of a signal output from at least one pixel among the plurality of first pixels, and outputs the second signal based on signal values of signals output from at least two pixels among the plurality of second pixels.

31. The detector according to claim 25, wherein a plurality of semiconductor substrates are tiled.

32. The detector according to claim 25, wherein the semiconductor substrate is a single crystal substrate made of cadmium zinc telluride.

33. The detector according to claim 25, wherein the semiconductor substrate is a single crystal substrate made of one of cadmium telluride, lead iodide, mercury iodide, bismuth iodide, and thallium bromide.

34. A radiation CT apparatus comprising:
the radiation detector according to claim 25;
a radiation generator configured to irradiate the radiation detector with radiation; and
a signal processor configured to process a signal output from the radiation detector.

* * * * *